US008721555B2

(12) United States Patent
Westbrook et al.

(10) Patent No.: US 8,721,555 B2
(45) Date of Patent: May 13, 2014

(54) METHOD FOR MEASURING CENTRAL VENOUS PRESSURE OR RESPIRATORY EFFORT

(75) Inventors: Philip R. Westbrook, Carlsbad, CA (US); Daniel J. Levendowski, Carlsbad, CA (US); Timothy Zavora, Carlsbad, CA (US); Djordje Popovic, Carlsbad, CA (US); Milenko Cvetinovic, Carlsbad, CA (US); Chris Berka, Carlsbad, CA (US)

(73) Assignee: Watermark Medical, Inc., Boca Raton, FL (US)

( * ) Notice: Subject to any disclaimer, the term of this patent is extended or adjusted under 35 U.S.C. 154(b) by 548 days.

(21) Appl. No.: 12/708,403

(22) Filed: Feb. 18, 2010

(65) Prior Publication Data

US 2010/0145201 A1 Jun. 10, 2010

Related U.S. Application Data

(63) Continuation of application No. 11/763,173, filed on Jun. 14, 2007, now Pat. No. 7,691,067.

(60) Provisional application No. 60/813,401, filed on Jun. 14, 2006.

(51) Int. Cl.
*A61B 5/02* (2006.01)

(52) U.S. Cl.
USPC .......................................... 600/485; 600/504

(58) Field of Classification Search
USPC .................. 600/309, 481–507, 561
See application file for complete search history.

(56) References Cited

U.S. PATENT DOCUMENTS

| 5,081,447 | A | | 1/1992 | Echols | |
|---|---|---|---|---|---|
| 5,368,026 | A | * | 11/1994 | Swedlow et al. | 600/323 |
| 5,381,801 | A | | 1/1995 | McShane | |
| 5,447,161 | A | | 9/1995 | Blazek et al. | |
| 5,941,837 | A | * | 8/1999 | Amano et al. | 600/595 |
| 6,122,538 | A | * | 9/2000 | Sliwa et al. | 600/407 |
| 6,600,949 | B1 | | 7/2003 | Turcott | |
| 6,641,571 | B2 | | 11/2003 | Redmond et al. | |
| 6,811,538 | B2 | * | 11/2004 | Westbrook et al. | 600/529 |
| 6,970,792 | B1 | | 11/2005 | Diab | |
| 7,081,095 | B2 | | 7/2006 | Lynn | |
| 7,117,028 | B2 | | 10/2006 | Bardy | |

(Continued)

OTHER PUBLICATIONS

Nilsson et al., Age and gender do not influence the ability to detect respiration by photoplethysmography, J Clin Monit Comput. Dec. 2006; 20(6):431-6. Epub Oct. 11, 2006.

(Continued)

*Primary Examiner* — Patricia Mallari
*Assistant Examiner* — Tiffany Weston
(74) *Attorney, Agent, or Firm* — Fiala & Weaver P.L.L.C.

(57) ABSTRACT

Photoplethysmography (PPG) is obtained using one red (e.g., 660 nm) and one infrared (e.g., 880 to 940 nm) light emitting diode with a single photo diode in combination with a pressure transducer thereby allowing both CVP and SpO2 to be measured simultaneously. The system also includes sensors capable of measuring position, angle and/or movement of the sensor or patient. Once the PPG signal is acquired, high pass adaptive and/or notch filtering can be used with one element of the filter from the red and infrared signals used to measure the arterial changes needed to compute SpO2 and the other element of the signal can be used to measure CVP changes.

14 Claims, 14 Drawing Sheets

(56) References Cited

U.S. PATENT DOCUMENTS

| | | | |
|---|---|---|---|
| 7,118,534 B2* | 10/2006 | Ward et al. | 600/490 |
| 7,691,067 B2 | 4/2010 | Westbrook | |
| 2002/0188205 A1* | 12/2002 | Mills | 600/481 |

OTHER PUBLICATIONS

Nilsson et al., Respiration can be monitored by photoplethysmography with high sensitivity and specificity ragardless of anaesthesia and ventilatory mode. Acta Anaesthesiol Scand. Sep. 2005; 49(8): 1157-62.

Nilsson et al., Macrocirculation is not the sole determinant of respiratory induced variations in the reflection mode photoplethysmographic signal. Physiol Meas. Nov. 2003; 24(4):925-37.

Nilsson et al., Respiratory variations in the reflection mode photoplethysmographic signal. Relationships to peripheral venous pressure. Med Biol Comput. May 2003;41(3):249-54.

Nilsson et al., Monitoring of respiratory rate in postoperative care using a new photoplethysmographic technique. J Clin Monit Comput. 2000; 16(4):309-15.

An algorithm for the detection of individual breaths from the pulse oximeter waveform. Leonard P, Grubb NR, Addison PS, Clifton D, Watson JN. J Clin Monit Comput. Dec. 2004;18(5-6):309-12.

How to use central venous pressure measurements. Magder S. Curr Opin Crit Care. Jun. 2005;11(3):264-70.

The effect of contacting force on photoplethysmographic signals, Teng XF, Zhang YT. Physiol Meas. Oct. 2004;25(5):1323-35.

Measurement of central venous pressure from a peripheral intravenous catheter in the lower extremity. Cox P, Johnson JO, Tobias JD, South Med J. Jul. 2005;98(7):698-702.

Monitoring of heart and respiratory rates by photoplethysmography using a digital filtering technique. Nakajima K, Tamura T, Miike H. Med Eng Phys. Jul. 1996;18.

Relation between respiratory variations in pulse oximetry plethysmographic waveform amplitude and arterial pulse pressure in ventilated patients. Cannesson M, Besnard C, Durand PG, Bohe J, Jacques D. Crit Care. Oct. 5, 2005;9(5):R562-8. Epub Aug. 23, 2005.

Estimation of respiratory volumes from the photoplethysmographic signal, Part 1: Experimental results. Johansson A, Oberg PA, Med Biol Eng Comput. Jan. 1999;37(1)42-7.

Estimation of respiratory volumes from the photoplethysmographic signal. Part 2: A model study. Johansson A, Oberg PA Med Biol Eng Comput. Jan. 1999;37(1):48-53.

Estimation of breathing interval from the photoplethysmographic signals in children. Foo JY, Wilson SJ. Physiol Meas. Dec. 2005;26(6):1049-58. Epub Oct. 31, 2005.

Neural network for photoplethysmographic respiratory rate monitoring. Johansson A. Med Biol Eng Comput. May 2003;41(3):242-8.

Noninvasive monitoring of respiratory mechanics during sleep. Farre R, Montserrat JM, Navajas D. Eur Respir J. Dec. 2004;24(6):1052-60.

Influence of tidal volume and thoraco-abdominal separation on the respiratory induced variation of the photoplethysmogram. Johansson A, Stromberg T. J Clin Monit Comput. 2000;16(8):575-81.

Effects of changes in central venous pressure on upper airway size in patients with obstructive sleep apnea. Shepard JW Jr, Pevernagie DA, Stanson AW, Daniels BK, Sheedy PF. Am J Respir Crit Care Med. Jan. 1996;153(1):250-4.

Technical protocol for the use of esophageal manometry in the diagnosis of sleep-related breathing disorders. Kushida C. Giocomini A, Lee M, Guilleminault C, Dement W, Sleep Med 3(2002) 163-173.

The influence of large subcutaneous blood vessels on pulse oximetry, Mannheimer P, O'Neil M, Konecny E. J Clin Monitor Comput 18:179-188, 2004.

Use of pulse transit time to distinguish respiratory events from tidal breathing in sleeping children. Foo J, Wilson S, Bradley A, Williams G, Harris M, Cooper D. Chest 2005; 128; 3013-3019.

Value of beat-to-beat blood pressure changes, deteced by pulse transit time, in the management of obstructive sleep apnea/hypopnea syndrome. Pitson D, Stradling J. Eur Respir J 1998:12:685-692.

Comparison of Esophageal Pressure with Pulse Transit Time as a measure of respiratory effort for scoring obstructive nonapneic respiratory events. Argod J, Pepin J, Smith R, Levy P. Am J Respir Crit Care Med vol. 162 (2000) 87-93.

Human cerebral venous outflow pathway depends on posture and central venous pressure. Gisolf J, Van Lieshout J, Van Heusden K, Pott F, Stok W, Karemaker J. J Physiol 560.1(2004), 317-327.

High central venous pressure is associated with prolonged mechanical ventilation and increased mortality after lung transplantation, D Pilcher, C Scheinkestel, G Snell, A Davey-Quinn, M Bailey, T Williams. J Thorac Cardiovasc Surg. 2005;129(4):912-8.

International Search Report/Written Opinion issued in PCTUS2007071242 on Mar. 13, 2008, 11 pages.

A Report by the American Society of Anesthesiologists Task Force on Perioperative Management of Patients with Obstructive Sleep Apnea, Practice Guidelines for the Perioperative Management of Patients with Obstructive Sleep Apnea. Anesthesiology, 2006. 104(5): p. 1081-1093.

Alemohammad, M., Z Khan, M Sanatkar, S Mirkhani, Ghorbandaie-Poure I., Pressure measurements during cardiac surgery—internal jugular vs. central venous. Middle East J Anestesiol. 2005; 18(2):357-65.

Aurell, J. and D. Elmqvist, Sleep in the surgical intensive care unit: continuous polygraphic recording of sleep in nine patients receiving postoperative care. Sr Med J (Clin Res Ed), 1985. 290(6474): p. 1029-32.

Benum0f. J.L., Obstructive sleep apnea in the adult obese patient: implications for airway management. Anesthesiology Clinics of North Arnerica, 2002. 20(4): p. 789-811.

Benumof, J.L., Obesity, sleep apnea, the airway, and anesthesia. Current Opinion in Anaesthesiology, 2004. 17(1): p. 21-30.

Brown, K.: Intermittent Hypoxia and the Practice of Anesthesia. Anesthesiology. 2009 110(4). p. 922-7.

Catley, DM., et al., Pronounced, episodic oxygen desaturation in the postoperative period: its association with ventilatory pattern and analgesic regimen. Anesthesiology, 1985. 63(1): p. 20-8.

Chung et al., A Systemic Review of Obstructive Sleep Apnea and Its Implications for Anesthesiologists, Ambulatory Anesthesiology, vol. 107, No. 5, Nov. 2008, pp. 1543-1563.

Cronin, A., et al., Opioid inhibition of rapid eye movement sleep by a specific mu receptor agonist. Br J Anaesth, 1995. 74(2): p. 188-92.

Den Herder, Cindy et al., Risks of General Anaesthesia in People with Obstructive Sleep Apnoea, BMJ, vol. 329, Oct. 23, 2004, pp. 955-959 and 1 cover sheet.

Deutscher, R., et al., OSA protocol promotes safer care. Anesthesia Patient Safety Foundation Newsletter 2002-2003: p. 58-60.

Ellis, B.W. and H.A. Dudley, Some aspects of sleep research in surgical stress. J Psychosom Res, 1976. 20(4): p. 303-8.

Finkel, K., et al., Obstructive Sleep Apnea: The Silent Pandemic. In ASA Annual Meeting. 2006. Chicago, IL.: 1 page.

Finkel, K., et al., The Silent Perioperative Pandemic. Sleep Review, 2006. 7(4): p. 56-60.

Gali, B.: Identification of Patients at Risk for Postoperative Respiratory Complications Using a Preoperative Obstructive Sleep Apnea Screening Tool and Postanesthesia Care Assessment. Anesthesiology. 2009 110(4). p. 869-77.

Gali, Bhargavi et al., Management Plan to Reduce Risks in Perioperative Care of Patients with Presumed Obstructive Sleep Apnea Syndrome, JCSM Journal of Clinical Sleep Medicine, vol. 3, No. 6, 2007, pp. 582-588.

Gentil, B., et al., Enhancement of postoperative desaturation in heavy snorers. Anesth Analg, 1995. 81(2): p. 389-92.

Gupta, R., et al., Postoperative complications in patients with obstructive sleep apnea syndrome undergoing hip or knee replacement: a case-control study. Mayo Clinic Proceedings, 2001. 76: p. 897-905.

Kaw, R., et al., Unrecognized Sleep Apnea in the Surgical Patient: Implications for the Perioperative Setting. Chest, 2006. 129(1): p. 198-205.

(56) References Cited

OTHER PUBLICATIONS

Keifer, J., et al.. Sleep Disruption and Increased Apneas after Pontine Microinjection of Morphine. Anesthesiology, 1992. 77(5): p. 973-82.
Kheterpal, Sachin et al., Prediction and Outcomes of Impossible Mask Ventilation, Anesthesiology, vol. 110, No. 4, Apr. 2009, pp. 891-897.
Knill, R., et al., Anesthesia with Abdominal Surgery Leads to intense REM Sleep during the First Postoperative Week. Anesthesiology, 1990. 73(1): p. 52-61.
Lickteig, Carla et al., Risks of OSA and Anesthesia, Sleep Review, Jan./Feb. 2003, 5 pages.
Loadsman, J. and D. Hillman, Anaesthesia and sleep apnoea. British Journal of Anaesthesia, 2001. 86(2): p. 254-266.
Lofsky, Ann, Sleep apnea and narcotic postoperative pain medication: a morbidity and mortality risk. Anesthesia Patient Safety Foundation Newsletter. Summer 2002:24-25.
Neligan, Patrick J. et al., Continuous Positive Airway Pressure via the Boussignac System Immediately after Extubation Improves Lung Function in Morbidly Obese Patients with Obstructive Sleep Apnea Undergoing Laparoscopic Bariatric Surgery, Anesthesiology, vol. 110, No. 4, Apr. 2009, pp. 878-884.
Oliver, Z. and V. Hoffstein, Predicting effective continuous positive airway pressure. Chest, 2000. 117(4): p. 1061-64.
Orr, W.C. and M.L. Stahl, Sleep disturbances after open heart surgery. Am J Cardiol, 1977. 39(2): p. 196-201.
Pembrook, Linda. High Risk for Sleep Apnear Found in Pain Patients on Opioids, Issue: Jun. 2006, vol. 32:06, 3 pages.
Ramachandran et al., A Meta-analysis of Clinical Screening Tests for Obstructive Sleep Apnea, Anesthesiology, Vo. 110., No. 4, Apr. 2009, pp. 928-939.
Reeder, M.K., et al., Late postoperative nocturnal dips in oxygen saturation in patients undergoing major abdominal vascular surgery. Predictive value of pre-operative overnight pulse oximetry. Anaesthesia, 1992. 47(2): p. 110-5.
Reeder, M.K., et al., Postoperative hypoxaemia after major abdominal vascular surgery. Sr J Anaesth, 1992. 68(1): p. 23-6.
Reeder, M.K., et al., Postoperative obstructive sleep apnoea. Haemodynamic effects of treatment with nasal CPAP. Anaesthesia, 1991. 46(10): p. 849-53.
Remmers, J.E., et al., Pathogenesis of upper airway occlusion during sleep. J Appl Physiol.: Respirat. Environ. Exercise Physiol., 1978. 44(6): p. 931-8.
Rock, P. and A. Passannante, Preoperative assessment pulmonary. Anesthesiology Clinics of North America, 2004. 22(1): p. 77-91.
Rosenberg, J. and H. Kehlet, Postoperative episodic oxygen desaturation in the sleep apnoea syndrome. Acta Anaesthesiol Scand, 1991. 35(4): p. 368-9.
Rosenberg, J., et al., Circadian variation in unexpected postoperative death. Br J Surg, 1992. 79(12): p. 1300-2.
Rosenberg, J., et al., Late postoperative nocturnal episodic hypoxaemia and associated sleep pattern. Br J Anaesth, 1994. 72(2): p. 145-50.
Rosenberg-Adamsen, et al., Postoperative sleep disturbances: mechanisms and clinical implications. Br J Anaesth, 1996. 76(4): p. 552-9.
Sabers, C., et al.: The diagnosis of obstructive sleep apnea as a risk factor for unanticipated admissions in outpatient surgery. Anesth Analg. May 2003;96(5):1328-35.
Sasse, S.A., et al., Timing of Changes in Oxyhemoglobin Saturation Resulting from Breath Holding. Sleep Medicine, 2006. 7 (S2): p. S46-7.
Standards and Practice Committee of the American Sleep Disorders Association. ASDA Standards of Practice, Practice Parameters for the Use of Portable Recording in the Assessment of Obstructive Sleep Apnea.. Sleep, 1994 17(4), p. 372-377.
Warner, David S. et al., Obstructive Sleep Apnea of Obese Adults, Anesthesiology, vol. 110, No. 4, Apr. 2009, pp. 908-921.
Westbrook P, et al. Predicting Effective Continuous Positive Airway Pressure (CPAP) based on Laboratory Titration and Auto-titrating CPAP, 8th World Congress on OSA. Sleep Medicine. vol. 7, Suppl. 2. 2006. 2 pages.
Westbrook P, et al. Predicting Treatment Outcomes for Oral Appliance Therapy for Sleep Apnea using Pre-treatment In-home Sleep Studies, 8th World Congress on OSA. Sleep Medicine. vol. 7, Suppl. 2. 2006. p. 1-2.
Westbrook, P., et al. Validation of an Apnea Risk Evaluation Questionnaire. in American Thoracic Society International Conference. 2005. San Diego, CA. 2 pages.
Westbrook, P., et al., Description and Validation of the Apnea Risk Evaluation System: A Novel Method to Diagnose Sleep Apnea-Hypopnea in the Home. Chest, 2005. 128(4): p. 2166-75.
Wilson, Kerryn et al., Can Assessment for Obstructive Sleep Apnea Help Predict Postadenotonsillectomy Respiratory Complications, Anesthesiology, vol. 96, No. 2, Feb. 2002, pp. 313-322.
Young, T., et al., Epidemiology of Obstructive Sleep Apnea: A Population Health Perspective. Am J Respir Crit Care Med, 2002. 165(9): p. 1217-39.
Obstructive sleep apnea syndrome: effect of respiratory events and arousal on pulse wave amplitude measured by photoplethysmography in NREM sleep. Haba-Rubio J, Darbellay G, Herrmann FR, Frey JG, Fernandes A, Vesin JM, Thiran JP, Tschopp JM. Sleep Breath (2005) 9: 73-81, revised to include date and page numbers.
Waldemar, Carlo et al., Alae nasi activation (nasal flaring) decreases nasal resistance in preterm infants. Pediatrics, Sep. 1983, vol. 72, Issue 3, pp. 338-343, Abstract.

\* cited by examiner

METHOD FOR MEASURING CENTRAL VENOUS PRESSURE OR RESPIRATORY EFFORT

RELATED APPLICATION

This application is a continuation application of U.S. patent application Ser. No. 11/763,173 filed Jun. 14, 2007, now U.S. Pat. No. 7,691,067, which claims the benefit of U.S. Provisional Applications Ser. No. 60/813,401, filed Jun. 14, 2006, titled A NOVEL METHOD FOR MEASURING CENTRAL VENOUS PRESSURE OR RESPIRATORY EFFORT which are hereby incorporated by reference in their entirety.

FIELD OF THE INVENTION

This invention relates to systems and methods for measuring, monitoring and analyzing physiological data including respiratory effort and central venous pressure.

BACKGROUND OF THE INVENTION

Normal Breathing

For air to flow into the lungs, the gas pressure in the gas exchanging units, the alveoli, must be lowered to below that at the airway opening. At the end of expiration, when there is no airflow, the pressure in the alveoli is the same as atmospheric. To get air into the lungs, the pressure in the chest surrounding the lungs, intrathoracic pressure, must be lowered to below atmospheric. This is accomplished by contraction of the inspiratory muscles which enlarges the thorax and further lowers the intrathoracic pressure (the intrathoracic or pleural pressure is already slightly sub-atmospheric due to the elastic recoil of the lungs and chest wall). The lower intrathoracic pressure expands the alveoli, thus lowering the intra-alveolar gas pressure below atmospheric so that air flows into the lungs.

Taking a breath requires that the inspiratory muscles generate sufficient force to overcome the elastic recoil of the lungs and chest wall, frictional lung and chest wall tissue resistance, and the frictional resistance to airflow through the airways. At the end of an inspiration, the potential energy stored in the tissues of the lungs and chest wall is available to allow rapid passive exhalation when the inspiratory muscles cease contraction and the distending force disappears. All intrathoracic structures, including the heart and great veins, are subjected to the pressures generated by breathing, either due to spontaneous or mechanical ventilation.

Measurement of Central Venous Pressure

During inspiration the central venous pressure (CVP) decreases, aiding the return of blood to the heart. Changes in pleural or intrathoracic pressure due to respiration are reflected by and can be timed to changes in central venous pressure. When recumbent, the internal and external jugular veins are open and provide the primary cerebral venous and superficial forehead venous return. The communication between the superior vena cava and the veins of the head allows intrathoracic pressure changes to be reflected by the superficial veins of the head. In a sense, the forehead veins offer a direct fluid filled catheter into the thoracic cavity, and when the correct compressive force is applied against the skull, respiratory effort linked venous pressure changes can be accurately measured. When upright, the jugular veins tend to collapse and venous outflow is distributed to the vertebral venous plexus for return.

The head is relatively highly vascularized and when a person is recumbent so that the vertical position of the optical sensors is close to that of the right atrium, venous pressure is about the same as the pressure in the superior vena cava. Thus the head and neck provide a number of sites that can be used for indirect measurement of CVP. These sites include but are not limited to the forehead (frontal, superficial temporal, supra-orbital, and angular veins), cheek (transverses facial vein), nose (nasal arch and supra labial) or neck (posterior external plexus). Indirect measurement of CVP may also be performed from any site on the body that has sufficient venous flow. For example, veins on the dorsum of the hand or cephalic or balisic veins of the arm may provide alternate sites for monitoring changes in CVP.

The most common method of monitoring CVP is by insertion of a central venous catheter, but this is not optimal for routine monitoring. Complications of central venous catheter placement include carotid artery puncture, pneumothorax, cardiac tamponade, arrythmias, and major air embolism. Infection is the major complication of prolonged central catheters. CVP can be obtained with transducers and electronic monitors, with a simple water manometer or, during clinical examination, by measuring jugular venous distension. Thus, any measure of CVP that can be performed either from the surface of the skin or non-invasively would be beneficial.

SUMMARY OF THE INVENTION

The present invention provides systems and method which collect and analyze physiological signals for various purposes. For some of the embodiments and aspects described below, references to the measurement of CVP or the means to measure CVP assume that CVP can also be used to measure or indicate respiration. Since there is a good correlation between the pressures of the right and left internal jugular veins with that of CVP; the term CVP may also be used to include jugular venous pressure, central venous pressure and right atrial pressure.

In a further aspect a sensor system capable of measuring respiration, SpO2 (or oxygen saturation) and pulse rate is integrated into an auto-adjusting Positive Airway Pressure device (APAP). In a further aspect, a sensor system capable of measuring respiration, SpO2 and pulse rate is integrated into a Continuous Positive Airway Pressure device (CPAP). In a further aspect, a sensor system capable of measuring respiration, SpO2 and pulse rate is integrated into a Variable Positive Airway Pressure device (VPAP). In a further aspect, a sensor system capable of measuring respiration, SpO2 and pulse rate is integrated into a bi-level Positive Airway Pressure device.

DETAILED DESCRIPTION

Figure 1A:
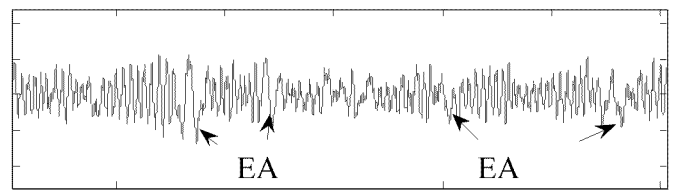
FIG. 1a presents the raw signal obtained using an 880 nm infrared emitter and FIG. 1b presents a slow wave component which includes distinctive effort arousal waves.

In a preferred sensor system embodiment, photoplethysmography (PPG) is obtained using one red (e.g., 660 nm) and one infrared (e.g., 880 to 940 nm) light emitting diode with a single photo diode in combination with a pressure transducer thereby allowing both CVP and SpO2 to be measured simultaneously. In another embodiment any optical wavelength capable of measuring venous pressure changes can be combined with a pressure transducer, pressure sensor or other device capable of measuring venous pulsation from the surface of the skin. In an alternative embodiment only a pressure transducer, pressure sensor or any other device capable of measuring venous pulsation from the surface of the skin is used. Rather than limiting the number of PPG and pressure sensors to one per system, an array of optical sensors, photodiodes and/or pressure transducers can also be used to improve the measurement of CVP or SpO2. Measurement of the amount of light reflected through the skin from multiple photodiodes can be useful in adjusting the amount of light applied to the LEDs to optimize signal quality. Alternatively the reflectance or pressure patterns obtained from a multiple sensor array, either from the same region of the head or body or from multiple locations on the body, may be used to adjust the amount of external force applied to the sensor and/or improve the accuracy of the CVP or SpO2 measure. Pressure sensors applied to multiple locations on the head and/or body may be useful in measuring or quantifying the CVP. For example the difference in the venous pressure changes at the internal jugular compared to the pulsation pattern obtained at the forehead may be useful in monitoring or diagnosing patients.

Although one embodiment only includes PPG or a pressure transducer, an alternative preferred embodiment includes sensors capable of measuring position, angle and/or movement of the sensor or patient. These measurements can be performed with accelerometers, tilt sensors or by other means and are generally referred to herein as position sensors. Because CVP is influenced by body location and body position, the pressure measurement can be calibrated or otherwise adjusted depending on this additional input. For example when ones head is on a couple of pillows in the supine position, the pressure transducer might be about 8 cm above the sternal angle, which would place it about 13 cm above the mid right atrium. In the lateral position with the same pillows, the transducer might be approximately 3 cm above the mid right atrium. The normal right atrial or central venous pressure is 5 to 10 cm H2O. Thus, when supine, it is likely that in a number of persons the forehead venous pressure might be of significantly lower amplitude. Knowing the exact head angle and position can be used to scale, calibrate or quantify the CVP results based on information unique to the patient or to a plurality of patients. Combining sensor position and angle information with the CVP data can be used to provide feedback when the sensor should be relocated, an additional sensor input should be added to the array or another sensor in the array should be the dominant input signal for calculating CVP. In applications when a limited number of sensors are appropriate, the combined information can be used to recognize factors contributing to poor signal quality and to indicate the need to relocate the sensor an alternative site (e.g., posterior base or lateral base of the neck) to obtain a better signal. Position, angle and movement sensors, such as accelerometers, are extremely sensitive to movements and when properly positioned and calibrated (e.g., near the forehead) can be used to detect subtle changes associated with normal or abnormal respiration. Movement or motion artifacts are also known to cause disturbances in physiological signals. Input signals that include information related to movement can be used as a reference signal that can be combined with an adaptive or notch filter to extract the artifact from the CVP signal and/or identify periods with artifact that should be excluded from analysis.

Venous pulsation can cause significant artifact when using PPG for reflectance pulse oximetry. Pressures between 60 and 80 mm Hg are preferable for optimal reflectance oximetry measurements. If insufficient pressure is applied to the reflectance sensor, the AC signal used to extract the pulse rate can become distorted (as a result of movement changes or venous pressure) and result in poor SpO2 accuracy. Alternatively, changes in venous pressure on the surface of the skin, being three to six times less than arterial pressure, can be difficult to accurately measure if excessive pressure was applied to the sensor against the skin. In the preferred embodiment, sufficient pressure is applied to optimize the measurement of the arterial changes using optical emitters (PPG) without eliminating the capability to measure venous changes with a pressure transducer. The optimum amount of pressure can also be achieved by using separate sensors for each of the physiological measures. Alternatively the force applied by the sensor against the skin can be distributed in a differential manner. For example, a means (i.e., directional grooves) can be incorporated above the pressure transducer to encourage drainage so that venous pressure changes can be measured.

In a preferred embodiment, a silicone interface between the pressure transducer and the skin provides a comfortable yet capable medium for transmitting changes in venous volume for measurement. The silicone can be medical grade. The thickness of the silicone above the pressure transducer can be adjusted to optimize the characteristics of the type of transducer. The durometer of the silicone can be adjusted to provide adhesive-like characteristics. The silicone durometer allows some compression so that it is comfortable against the skin when worn for extended periods with external force applied. For some medical applications, such as during surgery or anesthesia monitoring, the sensor would be disposable. In other applications, the sensor can be cleaned and reused.

In another embodiment, a means for regularly but briefly altering the compressing force applied to the optical sensor and thus to the underlying arteries would allow repeated measurements of arterial blood pressure. Blood pressure can be determined based on the amount of pressure needed to eliminate the arterial pulse pressure (i.e., when the amplitude of the red optical signal is abolished). The measurement of blood pressure in combination with CVP can have a number of critical care applications.

Obtaining a CVP Measure

Once the PPG signal is acquired, high pass adaptive and/or notch filtering can be used with one element of the filter from the red and infrared signals used to measure the arterial changes needed to compute SpO2 and the other element of the signal can be used to measure CVP changes. In a preferred configuration, the adaptive, notch or bandpass filtering accommodates between- and within-subject variability in breathing and heart rate to extract the highest quality elements for computation of SpO2 and CVP. The filter can be designed to be as sharp as possible and eliminate harmonic side effects. A single filtering step can be applied in real time or multiple filtering steps can be applied with computational processing resources are available. When filtering the input signal in an off-line mode, the processing can be completed in a single pass through data or further adaptive stages can be implemented with iterative processing of the signal.

The DC offset obtained from pressure transducer signal can be used to determine whether sufficient external pressure is being applied to the sensor to provide an accurate measure of SpO2 and/or CVP. In one embodiment, a temperature compensating pressure transducer is used so that the DC value does not change as a function of time against the skin. Alternatively changes in the DC value, either in nominal terms or in proportion to the venous pressure signal may be useful in assessing external pressure or placement. Alternative placement of the sensor may be needed to optimize the amplitude and/or accuracy of the PPG or pressure signals.

Figure 1B:
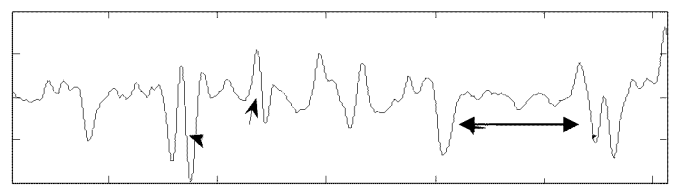
Figure 1C:
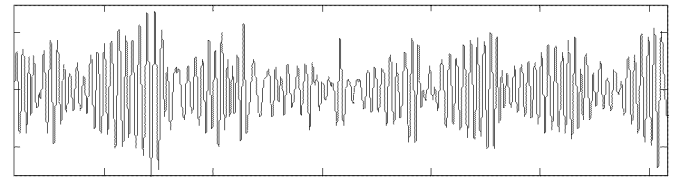
FIG. 1c presents the respiration signal (the oscillatory breathing component from the PPG signal corresponding to respiration) after removal of the EA-waves.
Figure 2:
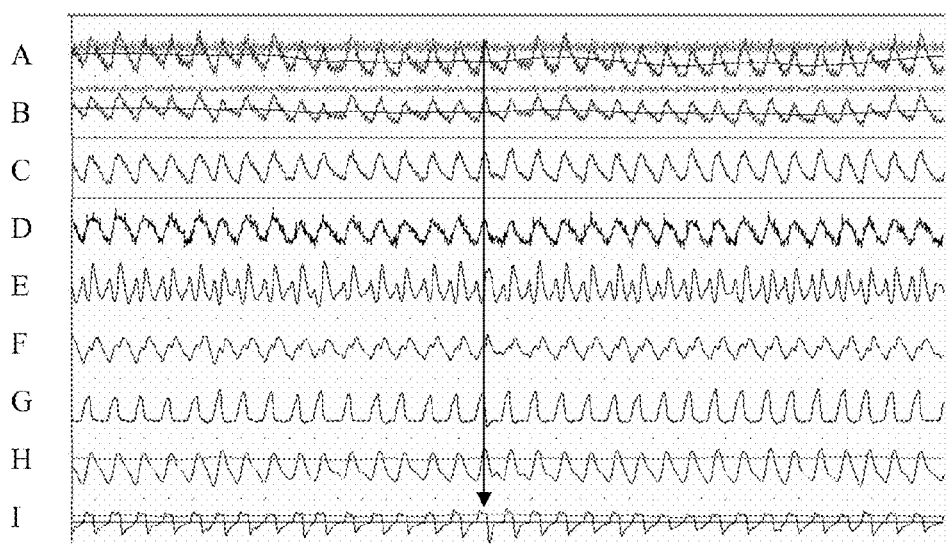
FIG. 2 presents several of the individual signals which could be used independently or combined to create a composite CVP signal.
Figure 3A:
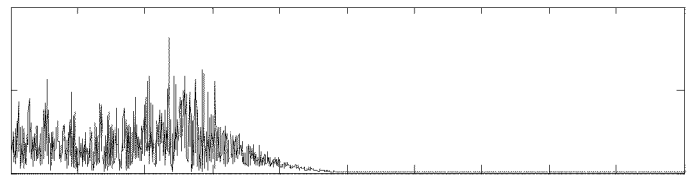
FIGS. 3a-c present the spectra characteristics from three signals that can be used to measure CVP.
Figure 3B:
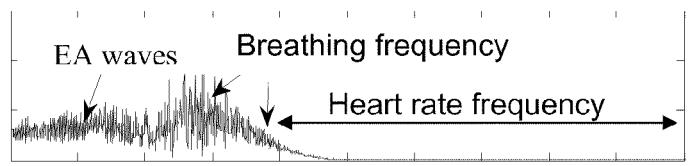
Figure 3C:
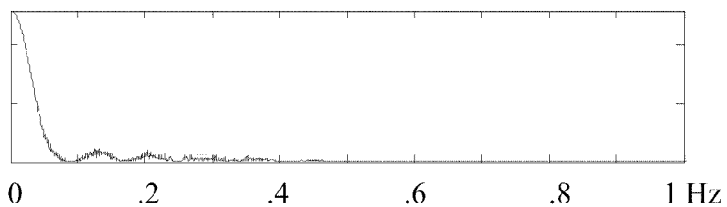

As mentioned previously, adaptive or notch high pass filters can be used to extract the venous pulsation signal obtained using optical emitters. Alternatively or simultaneously, sensor pressure signals can be acquired. The signals used to measure CVP can be analyzed in real time for purposes of real-time monitoring. Alternatively the signals can be recorded and analyzed off-line. Both sets of signals contain information with respect to central venous pressure and respiration. FIG. 1a presents the raw signal obtained using an 880 nm infrared emitter. FIG. 1b presents a slow wave component which includes distinctive effort arousal waves (EA-waves) that can be extracted with a filter from the CVP and appear when an obstructive breathing event is terminated. FIG. 1c presents the respiration signal (the oscillatory breathing component from the PPG signal corresponding to respiration) after removal of the EA-waves. FIG. 2 presents several of the individual signals which could be used independently or combined to create a composite CVP signal. These signals are compared to the current gold-standard for measuring respiratory effort, the esophageal balloon transducer and alternative measures of respiration using conventional effort bands. The Figure represents a 180-second epoch presenting the four intermediate signals available for use in the computation of FVP/RM (photoplethysmography from infrared and red optical signal, forehead pressure, and accelerometer), three conventional respiratory signals used in PSG (i.e., ribcage (chest) and abdomen piezo belt and esophageal balloon), and the preliminary composite effort signal derived from the intermediate signals and airflow by nasal pressure. FIGS. 3a-c present the spectra characteristics from three signals that can be used to measure CVP. The power spectra distribution from the (FIG. 3a) infrared and (FIG. 3b) red PPG signals, and (FIG. 3c) the forehead pressure transducer in a frequency range from 0 to 1 Hz in 0.1 Hz increments are shown. In this example the breathing frequency of this subject was 0.28 Hz (corresponding to ~18 breaths per minute). From these plots it is apparent the type of filters and filter settings that would be needed to extract the information pertaining to CVP/respiration, EA-waves, and pulse rate from signals obtained by PPG (e.g., infrared or red emitters) and sensor pressure.

Figure 4:
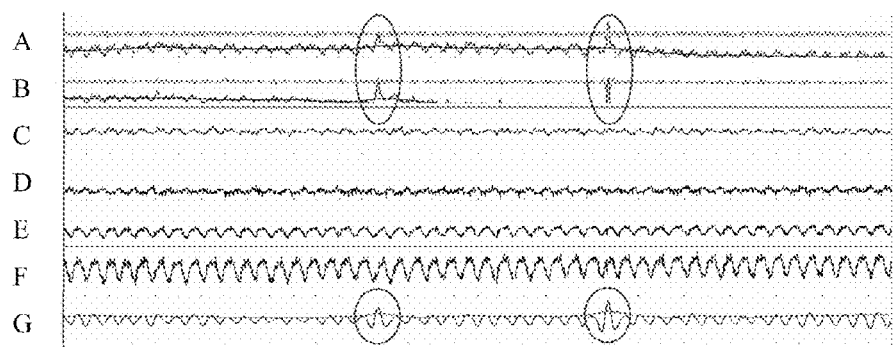
FIG. 4 provides an example where the CVP information from the 3-dimensional accelerometer data is of relatively poor quality while the information from the forehead pressure signal is robust.

Although the PPG and sensor pressure signals are highly correlated and can be acquired and applied independently, there is benefit in acquiring and combining the information from multiple sensors for purposes of monitoring CVP. When venous pulsation as measured by the sensor pressure signal may not be as strong when the patient is supine (due to gravitational effects on venous drainage). FIG. 4 provides an example where the CVP information from the 3-dimensional accelerometer data is of relatively poor quality while the information from the forehead pressure signal is robust. This is result of the patient being in the supine position. In FIG. 4 the patient is lateral left; the quality of forehead pressure signal is poor and the amplitude of the head movement associated with respiration is substantially greater in tilt 3 as compared to tilts 1 and 2. Specifically, the amplitude from one of the three accelerometer channels (tilt 3) is 10 times larger (scale adjusted) than the amplitude from tilts 1 and 2 as well as the forehead pressure signal. The two large amplitude changes in the IR and red signals cause minor artifact in the composite effort signal.

Figure 5:
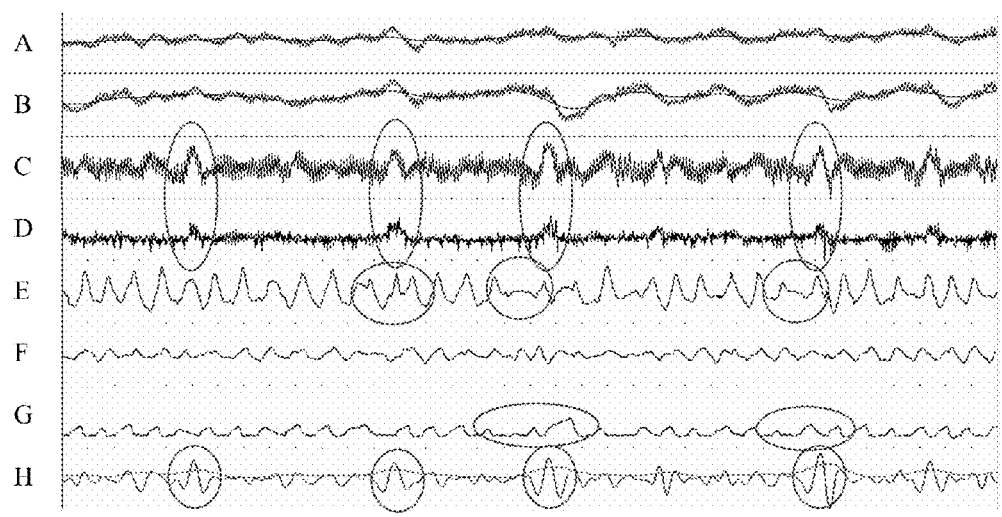
FIG. 5 presents a pattern that includes both artifact or physiological changes. Example of each of the input signals, infrared (A) and red (B) optical signals, forehead pressure (C), accelerometer (D), compared to the chest (E), abdomen (F) and esophageal balloon (G) signals and the composite FVP/RM signal (H) during supine in a worst case scenario. Both the esophageal balloon and abdomen signals are also very low amplitude. Note the disruptions in the forehead pressure, chest, esophageal an FVP/RM signals which are recognized in the accelerometer signal.

Once the composite signal is optimized the next step is to remove artifacts. In FIG. 4, for example, there is a significant amplitude change in the two optical signals that is reflected in the composite effort that appears to be artifact. FIG. 5 presents a pattern that includes both artifact or physiological changes. The forehead pressure and accelerometer signal provide information inconsistent with the optical signals, indicating a physiological event rather than an artifact. These patterns are confirmed by changes in the chest (rib-cage) effort and an increase in the esophageal balloon amplitude. Both the esophageal balloon and abdomen signals are also very low amplitude. Additional signal processing steps can be employed to improve the accuracy of the CVP signal(s). The identification and elimination of outliers that may be attributed to artifact, for example, can improve the quality of the signal. Recognition of periods when the signal is within normal ranges vs. when the signal is abnormal vs. when the signal is trending into an abnormal range can be important for monitoring or diagnostic purposes. To recognize these events simple statistical procedures such as mean, standard deviation or z-score techniques or empirically derived thresholds based on known acceptable ranges or patterns of the signal can be employed. Alternatively, more complicated linear or non-linear statistical or signal processing techniques such as discriminant function, fuzzy logic, neural network, wavelet, or fast-Fourier transforms can be applied. Correlation analysis can also be used to compare the shape or pattern of the signal to known values or a reference signal. Values that exceed the standard deviation, z-score or threshold can be eliminated, interpolated across or reduced to the appropriate range.

Figure 6:
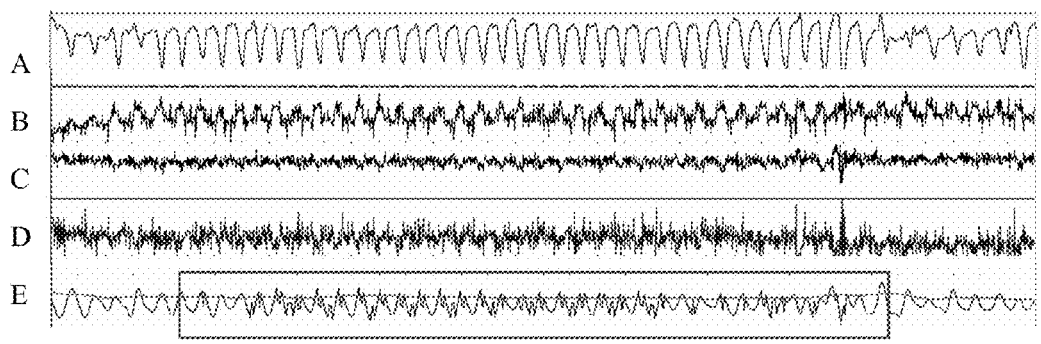
FIG. 6 presents a pattern where artifact enters the composite effort signal from the optical channels because of less than optimal application of adaptive filtering. The forehead pressure signal (A) is high amplitude and robust while the three accelerometer signals (B-D) are of low quality. Artifact enters the composite effort signal (E) from the optical channels because it takes approximately 2 minutes for the adaptive filter to adjust to a significant change in pulse rate.

Another signal processing procedure is to ensure that pulse rate artifact gets completely filtered, especially when the venous pulsations in the intermediate signals is low. In FIG. 6, for example, artifact enters the composite effort signal from the optical channels because of less than optimal application of adaptive filtering. The three accelerometer signals are of low quality however the forehead pressure signal is high amplitude and robust. Artifact enters the composite effort signal from the optical channels because in one example it takes approximately 2 minutes for the adaptive filter to adjust to a significant change in pulse rate. Prior to the averaging routine which will create the composite CVP signal, the amplitudes of the intermediate signals should be evaluated to select the one that appears most robust. In FIG. 6, for example, the forehead pressure signal would be an optimal candidate. This signal would then be used as the reference to adjust the frequency of an adaptive filter applied to the composite signal to remove pulse rate artifacts.

Figure 8:
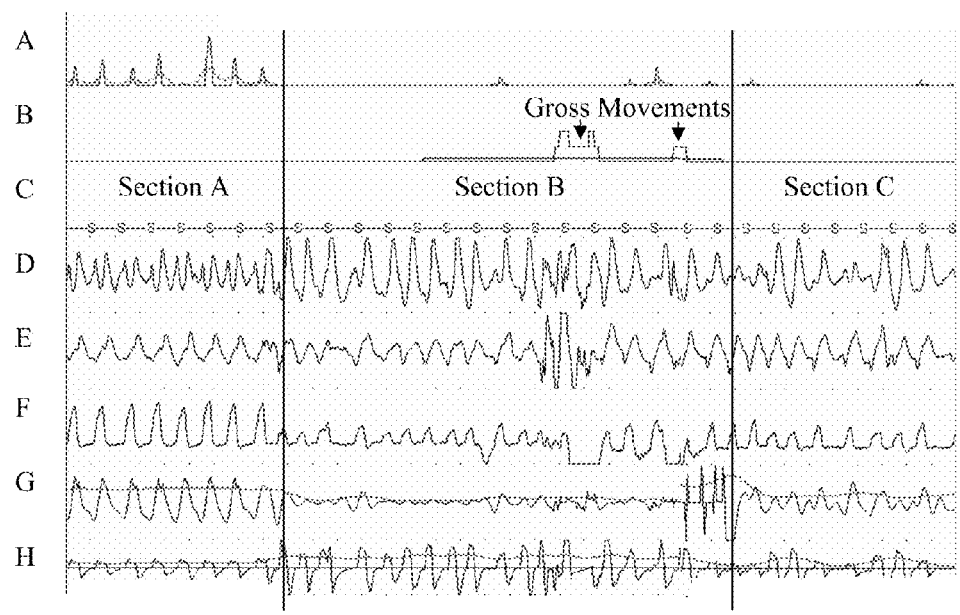
FIG. 8 presents an example when the amplitude of the CVP signal dramatically changes as a result of a decrease in respiratory effort unrelated to a head position change.

Once the artifacts are extracted, the amplitude of the signal can be scaled to provide a more quantified measure. FIG. 8 presents an example when the amplitude of the CVP signal dramatically changes as a result of a decrease in respiratory effort unrelated to a head position change. In section A, the FVP/FM (A-Effort) provides an equivalent measure as the esophageal balloon and a cleaner signal than the chest effort band. At the start of section B, the snoring abruptly stops and the amplitude of the esophageal balloon and A-Effort decrease substantially. Sections B and C are equivalent except that A-Effort signal is scaled to higher amplitude in section C to demonstrate that the FVP/RM signal still reflects respiration. Composite FVP/FM derived from red and IR optical and forehead pressure signals. The example shows that the reduction in amplitude of the CVP signals was substantially greater than the esophageal balloon. Without an adjustment in amplitude/scale, the appearance of respiration in the CVP signal is hardly distinguishable. However, when the amplitude of the CVP signal is increased, as shown in section C, respiration will be accurately measured. The amplitudes of the signals presented in FIG. 8 have been scaled to provide the best impression. From a visual impression, the CVP signal (A-effort) appears to provide a better representation of respiratory effort as compared to the esophageal balloon as compared to the two effort signals (chest and abdomen).

Figure 9A:
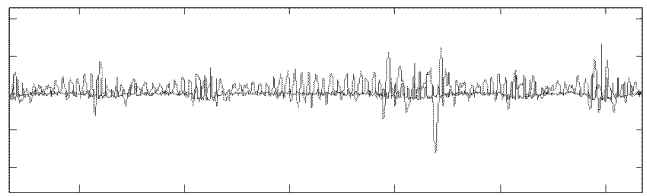
FIG. 9a presents a composite signal with the amplitudes from the infrared and red PPG and sensor pressure signals averaged.
Figure 9B:
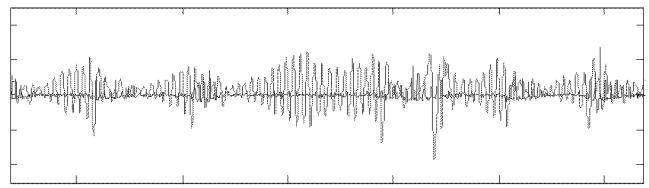
FIG. 9b presents an optimized composite signal after application of an averaging technique that accentuates the signals with the strongest amplitudes for both the CVP and EA-wave components FIGS. 10a and 10b provides examples of sleep disordered breathing with both the airflow and the composite CVP signal for a 600-second and a 100-second period, respectively.
Figure 10A:
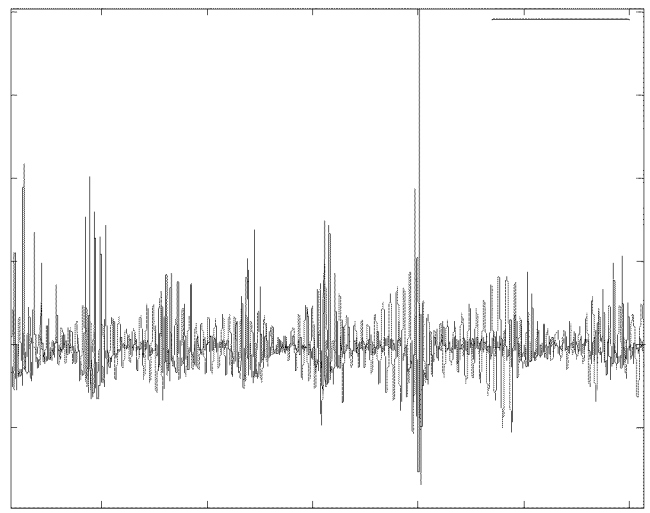
Figure 10B:
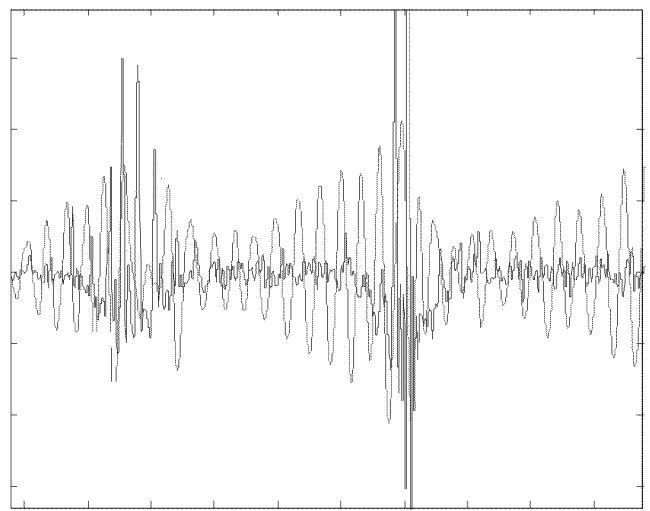

The EA-waves that identify the arousal from an obstructive breathing event and can be used to differentiate obstructive from central sleep apnea are more apparent in the sensor pressure signal when supine. FIG. 9a presents a composite signal with the amplitudes from the infrared and red PPG and sensor pressure signals averaged. The breathing cycles are visible, but EA waves are prominent. FIG. 9b presents an optimized composite signal after application of an averaging technique that accentuates the signals with the strongest amplitudes for both the CVP and EA-wave components (hereafter referred to as composite CVP). FIGS. 10a and 10b provides examples of sleep disordered breathing with both the airflow and the composite CVP signal for a 600-second and a 100-second period, respectively. Notice the characteristic increase in CVP during the period with a cessation in airflow.

Figure 11A:
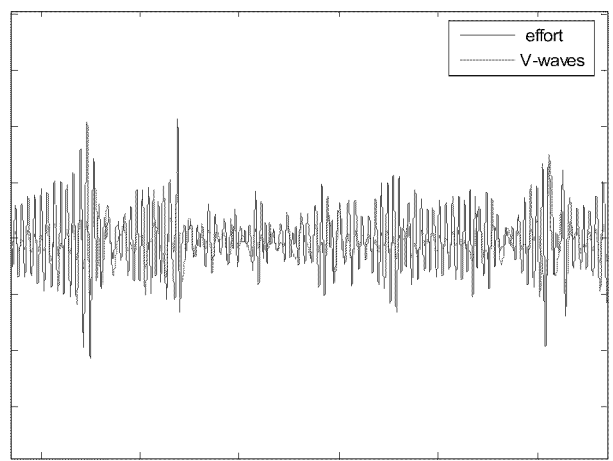
FIGS. 11a and 11b present the composite CVP with the EA-waves extracted and superimposed on the respiration signals.
Figure 11B:
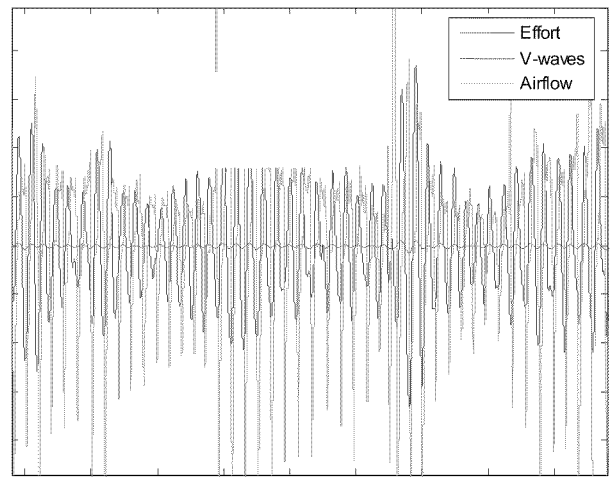
Figure 12A:
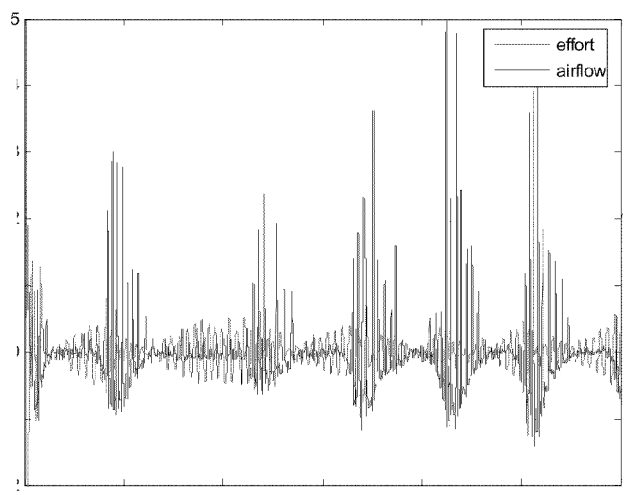
FIG. 12a presents patterns of airflow and composite effort for obstructive apnea breathing and FIG. 12b presents patterns of airflow and composite effort for central apnea.
Figure 12B:
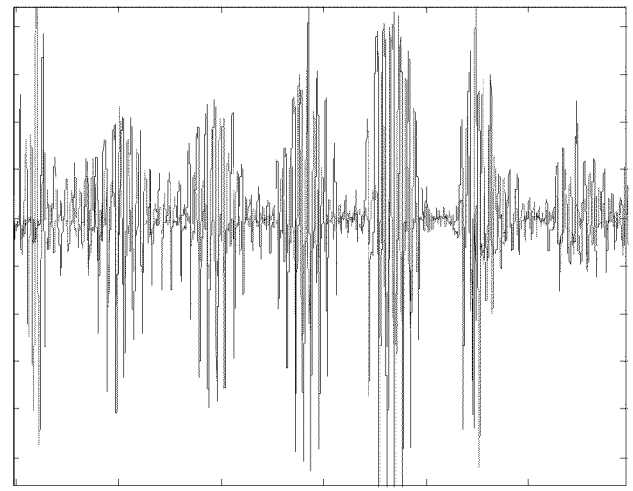

FIG. 11a presents the composite effort signal with the AE-wave arousal signal extracted and superimposed for a patient with central apnea and FIG. 11b presents the composite effort, EA-waves and airflow for the patient with central apnea. FIG. 12a presents patterns of airflow and composite effort for obstructive apnea breathing and FIG. 12b presents patterns of airflow and composite effort for central apnea. The patterns of airflow and optimized CVP associated with obstructive (FIG. 12a) vs. central apneas/hypopneas (FIG. 12b) are distinct. Note for obstructive breathing the effort signal is significantly greater than the airflow signal during the apnea period. For central events, the airflow and effort signals have similar amplitudes. The EA-wave is not apparent with central apnea, confirming the EA-wave as a unique independent measure of obstructive breathing during sleep.

Applications for Sensor Systems

In Conjunction with CPAP Treatment: Conventionally, the amount of fixed pressure needed for a Continuous Positive Airway Pressure device to treat obstructive sleep apnea (OSA) is determined during a laboratory titration study. As an alternative, auto-adjusting Positive Airway Pressure device (APAP) have been used to determine the effective pressure and to treat OSA. For APAP the airflow signal is analyzed to determine when the pressure should be adjusted. One of the limitations of the use of APAP to determine the pressure setting is that the patient is not usually monitored to determine what type of sleep disordered breathing is occurring. A patient initially diagnosed and treated for primarily obstructive apnea may experience respiratory control instability with periodic breathing (i.e., central sleep apnea) once the obstructive breathing is resolved. This is more common in patients with heart disease or congestive heart failure. It is generally agreed that an airflow signal and a measurement of respiratory effort is required to discriminate obstructive from central apneas.

The benefits of a sensor system capable of measuring respiration, SpO2 and pulse rate that can be easily integrated into an APAP, Continuous Positive Airway Pressure (CPAP), Variable Positive Airway Pressure (VPAP), or bi-level Positive Airway Pressure (Bi-PAP) device (hereafter referred to as PAP) are numerous. For example, the combination of respiratory effort, effort related arousals, and high resolution SpO2 may be an alternative to airflow in determining the effective pressure. When effort increases and SpO2 begins to drop, the PAP pressure can be automatically increased. When the EA-wave disappears, the pressure can be decreased. Alternatively, if the airflow does not recognize resistance (thus triggering an increase in pressure) but the SpO2 and effort are stable (i.e., suggesting a mask leak), the adjustment algorithm can utilize this information to avoid increasing the pressure to the point of causing a patient complaint. Alternatively, the combination of airflow, respiration and/or SpO2 can be used to identify patients with Cheyne-Stokes breathing after treatment with APAP or CPAP so that a variable PAP can be prescribed. The sensor system can be used as an independent measure of effort and SpO2 to confirm that the APAP device is providing the proper pressure. Alternatively, the sensor system can be used to obtain physiological information to assist a physician determine if the fixed CPAP pressure is still effective.

Control of Neuro-muscular Stimulators: A number of devices have been proposed to limit the collapse of the pharynx during sleep through the use of implantable neuro-muscular stimulators. The simplicity of this sort of implantable device is compromised because an effort band(s) around the torso is currently needed to time the stimulation to respiration. The sensor system can provide the feedback mechanism while simultaneously monitoring treatment efficacy through the use of the pulse oximetry signal.

Central Venous Pressure Monitoring and Mechanical Ventilation: As has been previously noted, mean CVP is determined by the function of the right heart and the pressure of venous blood in the vena cava. Under normal circumstances an increased venous return results in an augmented cardiac output without significant changes in venous pressure. However with poor right ventricular function or an obstructed pulmonary circulation, the right atrial pressure and CVP rises. Loss of blood volume or widespread vasodilation will result in reduced venous return and a fall in CVP. Cardiac output is determined by preload (CVP), afterload, heart rate and contractility. So even if CVP stays constant, cardiac output can be influenced by changes in the other three factors. However, while CVP alone cannot tell the whole story, it can give a good approximation of the hemodynamic status and right-sided cardiac function of a patient.

So CVP is frequently used to estimate circulatory function, in particular cardiac function and blood volume. While the CVP does not measure either of these directly, when taken in the context of other physical signs useful information can be gained. The supply of blood to the systemic circulation is controlled by the left ventricle. In normal patients the CVP closely resembles the left atrial pressure both during spontaneous ventilation and during mechanical ventilation and is often used to predict it.

For most critical care conditions requiring mechanical ventilation, such as lung injury or sepsis, measurement of CVP can provide important information. The CVP should be measured in patients with hypotension who are not responding to basic clinical management, continuing hypovolemia secondary to major fluid shifts or loss, and patients requiring infusions of inotropes. In a study of 1000 patients with acute lung injury fluid management was based on a treatment algorithm that had as a goal a central venous pressure of 10 to 14 mm HG in a liberal-strategy group compared to a goal of 4 mm Hg or less in the conservative—strategy group. The conservative strategy group had significantly better outcomes. A high CVP is also associated with an adverse outcome in patients following lung transplantation. Measurement of CVP is considered critical in resuscitation of patients with sepsis. CVP changes can be used in the detection of patient-ventilator asynchrony during low tidal volume ventilation.

Clinical Applications for CVP Measurements

Raised CVP can result from increased intrathoracic pressure, impaired cardiac function (only useful for information regarding the right side of the heart), hypervolaemia and superior vena cava obstruction. Low CVP is associated with hypovolaemia and reduced intrathoracic pressure (e.g., inspiration). The CVP measurement can be used for trend analysis and in monitoring treatment, possibly with some interpretation of initial or isolated measurements.

For example, in the ventilated neonate with respiratory distress a CVP of zero, is likely to be associated with hypovolaemia and inadequate right ventricular preload. A high CVP may be due to fluid/volume overload or congestive heart failure. In term babies with heart failure and pulmonary hypertension, higher pressures are found, so a value of 3 mm Hg may also indicate inadequate preload.

It needs to be remembered that CVP is related not only to the volume of intravascular blood within the venous system and the function of the cardiac pump, but also in intra-thoracic pressure. High CVP measurement may be artificially high, due to raised intra-thoracic pressure secondary to pneumothorax or over ventilation of compliant lungs. Inferior vena cava pressure reliably predicts right atrial pressure in pediatric cardiac surgical patients.

Alternative Measures of Respiratory Effort

Esophageal Manometry: The most accurate and direct method of measuring changes in intrathoracic pressure has been to measure esophageal pressure. The esophagus is a thin walled muscular tube that, from the point of view of the pulmonary physiologists, is ideally placed in the thoracic cavity between the lung surface and the chest wall. Although it has slight tone when relaxed, a differential pressure transducer connected to a tube placed in the esophageal lumen accurately reflects changes in intrathoracic pressure. Measurement of esophageal pressure during sleep has become the gold standard for detecting and quantifying inspiratory effort. Lack of inspiratory effort during an apnea defines a central apnea, and increasing effort without increasing flow (flow limitation), when terminated by an arousal, defines a RERA.

Placement of an esophageal catheter is done via the nose or mouth. The procedure is invasive, somewhat time consuming, and requires that the person placing the catheter be trained in the technique. It is not always well tolerated by the patient. It adds significantly to the cost of a polysomnogram (PSG). For these reasons it is not performed, or not routinely performed, in most Sleep Disorders Centers, and is not an option for portable (home unattended) monitoring.

Thoracic Cage Volume Changes: Instead of esophageal manometry, the most frequently used method of monitoring respiratory effort is to record thoracic cage expansion. Typically bands are placed around the chest and abdomen, and the change in circumference of these two compartments with breathing is measured. Inductive plethysmography, piezo electric crystals, conductive elastomere, and polyvinylidine fluoride film, magnetometers and strain gages have all been used. Properly calibrated, these devices can yield a reliable measure of inspiratory volume change (tidal volume). Lack of volume change can be equated with lack of effort, and rib cage/abdomen paradoxical motion can indicate effort against a closed or partially collapsed airway. However the devices are usually not calibrated, and may not stay in calibration during the night, so the information they give about effort is mostly qualitative. Rib cage and abdomen bands are generally comfortable and do not require special training to apply, but still are not easily self-applied by patients.

Pulse Transit Time: Pulse transit time (PTT) measures the time it takes for a pulse pressure wave to travel from the aortic valve to the periphery. The electrocardiographic R wave is used as the start-time, and the arrival of the pulse at the finger is determined with a finger photoplethysmograph. The PTT is inversely correlated to arterial blood pressure and has been shown to reflect the blood pressure fluctuations induced by negative pleural pressure swings.

Respiratory Muscle Electromyogram: Diaphragmatic electromyography (EMG) measured transcutaneously can provide a measure of inspiratory effort and has been shown to have a good correlation with increases in esophageal pressure.

Description of Sleep Disordered Breathing as it Relates to Respiration and CVP

In persons with sleep apnea, two major types of apnea events have been defined, central and obstructive. Both require a cessation of airflow for 10 seconds or more. In central apneas the lack of airflow is due to lack of respiratory effort. In obstructive apneas effort to breathe continues, but airflow is prevented by an occluded upper airway. Mixed apneas can also occur, where the initial component is due to lack of respiratory effort but the subsequent portion of the apnea is a result of airway obstruction.

Figure 13:
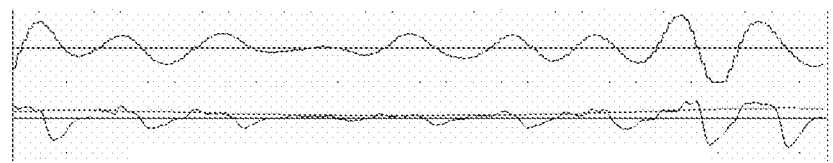
FIG. 13 presents a 30-second snapshot of a RERA with the top signal being the composite FVP/RM signal and the bottom signal being airflow.
Figure 14:
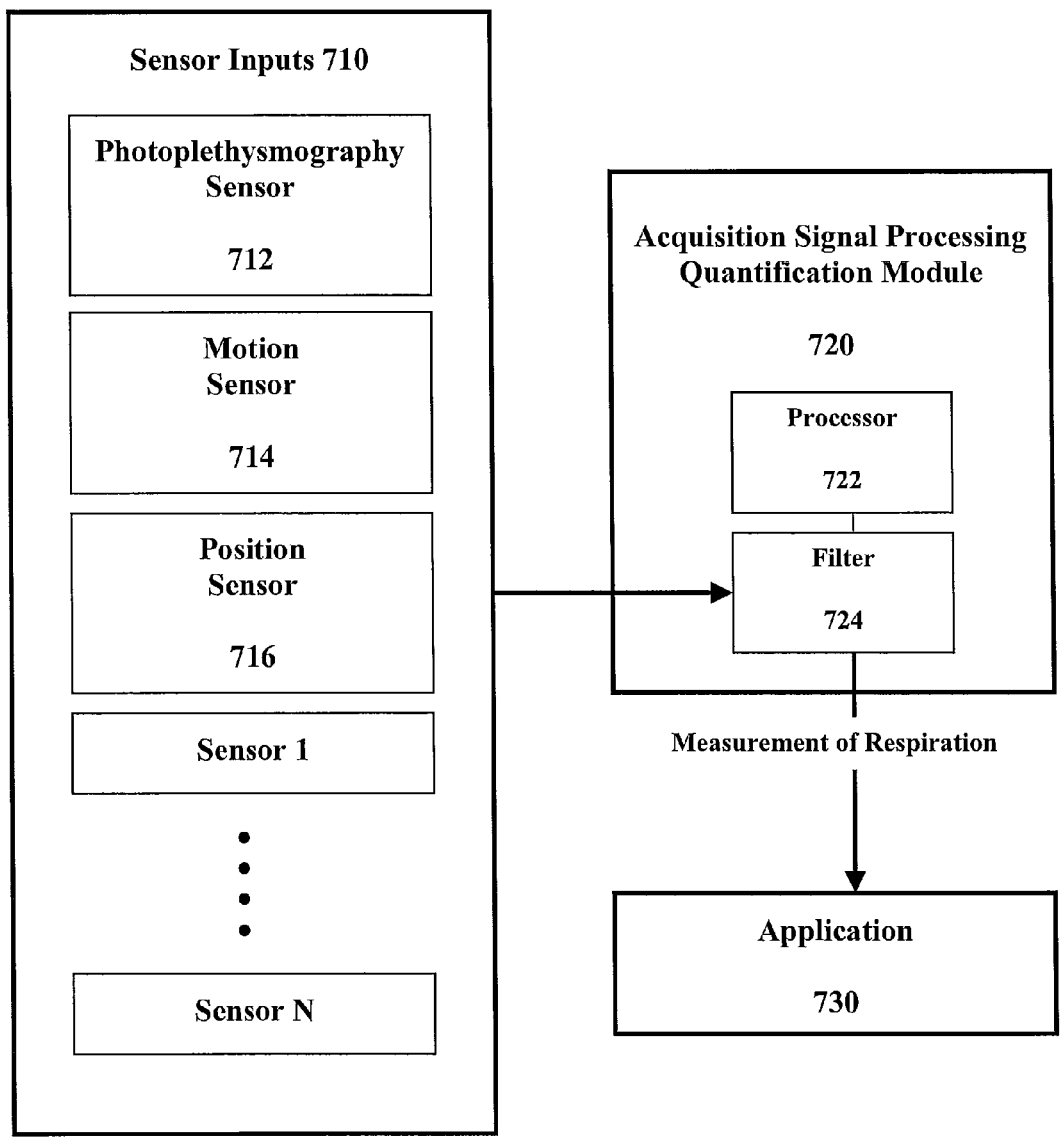
FIG. 14 is a block diagram of a system for measuring central venous pressure in accordance with an example embodiment.

Hypopneas, events with abnormally decreased but not absent airflow, can also be central, obstructive or mixed. Most definitions of hypopneas require a fall in oxyhemoglobin desaturation, but recently subtle obstructive events without a defined desaturation, characterized by increasing respiratory efforts against a partially closed airway and terminated by an arousal, have been described. These are called Upper Airway Resistance Events or Respiratory Effort Related Arousals (RERAs). By definition the absolute identification of central versus obstructive apneas and of RERAs requires measurement of inspiratory effort. FIG. 13 presents a 30-second snapshot of a RERA. The flattening of the FVP/RM signal flattens at the lowest point of the flow event, the increase in amplitude of the effort corresponds with the increase in snoring (A-Snore). This event is terminated with a head movement and pulse-rate arousal; it would be expected that the EA-wave would provide an additional confirmation of the arousal.

System Description

Figure 7:
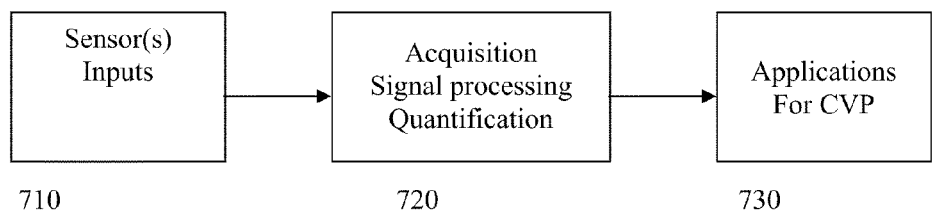
FIG. 7 is a block diagram of a generalized system for computing and utilizing CVP to implement the various systems and uses.

A generalized system for computing and utilizing CVP to implement the various systems and uses described above is represented in the functional block diagram presented in FIG. 7. The system can include any combination of the non-invasive sensors described above (e.g., optical sensors and detectors needed to acquire PPG, pressure sensors, accelerometer sensors, etc.) or array of sensors as was described above and represented generally by the block labeled "Sensor(s) Inputs" 710. The sensors provide signals to the "Acquisition Signal processing Quantification" block (data acquisition block) 720. That module or block can include electronic components, such as a micro processor, power supply, amplifiers, analog to digital converters, memory storage and other electronic circuits and components. The Acquisition Signal processing Quantification block also includes one or more modules which extract the CVP signal or information from the received signals and transform it as required to extract the discrete CPV information required for the specified application. Such extraction can be implemented, for example as software or firm ware running on a processor. Specified applications of the CVP information are generally represented by the block labeled "Applications for CVP" 730 and can be any one or more of the applications for CVP mentioned above. In one embodiment the CVP information is then incorporated into a user interface which can include presentation of the information on a visual display such as an LCD, LED or other display. The CVP information can also be stored for off-line analysis or utilized for real time monitoring.

The three components of the CVP system represented in FIG. 7 can be incorporated in multiple combinations of form factors depending on the application. Example applications have been described above. For example, the sensors and data acquisition components can be incorporated into a recorder and worn during sleep. The signal processing and quantification/analysis routines can be performed on a PC workstation with the results optionally presented on a computer monitor. In the preferred embodiment, there are no wires between elements that are affixed to the patient and elements that are not affixed to the patient. This minimizes artifact contamination from the lead wires moving or coming disconnected. In one embodiment, the three elements of the block diagram can be incorporated into a single unit that includes a module which monitors the information in real time. Preferably a single unit is be worn by the patient, such as being affixed to the forehead, or elements of the system can be affixed to the patient in a single location. If multiple sensors or sensor arrays are affixed to the patient, the interconnections between the elements can be made with a flex circuit or other interface that improves comfort and reduces the use of lead wires when possible. In another embodiment, wireless transmission of the signal inputs or CVP outputs is used to simplify the user interface.

Those of skill in the art will appreciate that the various illustrative blocks, modules and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules and method steps described in connection with the embodiments disclosed herein can be implemented or performed with a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention.

The invention claimed is:

1. A non-invasive system for measuring central venous pressure, the system comprising:
   a photoplethysmography sensor and a pressure sensor adapted to be placed on a patient's skin;
   wherein the photoplethysmography sensor generates a photoplethysmography signal, and the pressure sensor generates a pressure signal which comprises an element for determining central venous pressure information
   a motion sensor which generates a motion signal comprising an indication of one or more changes in a position of the patient; and
   an acquisition signal processing quantification module in communication with the photoplethysmography sensor, the pressure sensor, and the motion sensor and configured to
   filter the photoplethysmography signal, and
   use the photoplethysmography signal, the pressure signal, and the motion signal to determine a measurement of respiration, the measurement of respiration relating to central venous pressure.

2. The system of claim 1, further comprising:
   a position sensor which generates a position signal comprising a position of the patient's body;
   wherein the acquisition signal processing quantification module is in communication with the position sensor and is further configured to use the photoplethysmography signal, the motion signal, and the position signal to determine the measurement of respiration.

3. The system of claim 2 wherein the measurement of respiration comprises discrete central venous pressure information, the position signal comprises a position of the patient's head, and the acquisition signal processing quantification module is further configured to use changes in the position of the patient's head to extract the discrete central venous pressure information from the photoplethysmography signal.

4. The system of claim 2 wherein the acquisition signal processing quantification module is further configured to filter the photoplethysmography signal to extract effort arousal waves.

5. The system of claim 2 wherein the position signal comprises an indication of the position, angle and movement of the position sensor.

6. The system of claim 1, wherein the measurement of respiration comprises a measurement of central venous pressure.

7. The system of claim 6, further comprising an application in communication with the acquisition signal processing quantification module, wherein the application is configured to:
   receive the measurement of central venous pressure; and
   identify an apnea based on the measurement of central venous pressure.

8. The system of claim 7, wherein the application is further configured to generate a control signal for a positive airway pressure ventilation device based on the identified apnea.

9. The system of claim 7, wherein the identification of the apnea comprises discriminating between obstructive, central, and mixed apneas.

10. The system of claim 9, wherein the application is further configured to:
   receive a measurement of airflow; and
   use the measurement of central venous pressure and the measurement of airflow to discriminate between obstructive, central, and mixed apneas.

11. The system of claim 1, wherein the measurement of respiration comprises a composite measurement of central venous pressure, and the system further comprises a plurality of additional sensors which generate a plurality of intermediate signals comprising measurements of venous pulsation, wherein the acquisition of signal processing quantification module is in communication with the plurality of additional sensors and is further configured to use the photoplethysmography signal, the plurality of intermediate signals, and the motion signal to determine the composite measurement of central venous pressure.

12. The system of claim 11, wherein the acquisition signal processing quantification signal module is further configured to:
   select one or more reference signals from among the photoplethysmography signal and the plurality of intermediate signals; and
   use the one or more reference signals to remove artifacts from the composite measurement of central venous pressure.

13. A non-invasive system for measuring central venous pressure, the system comprising:
   a photoplethysmography sensor and a pressure sensor adapted to be placed on a patient's skin;
   wherein the photoplethysmography sensor generates a photoplethysmography signal, and the pressure sensor generates a pressure signal which comprises an element for determining central venous pressure information;
   a motion sensor which generates a motion signal comprising an indication of one or more changes in a position of the patient;
   a position sensor which generates a position signal comprising one or more positions of the patient; and
   an acquisition signal processing quantification module in communication with the photoplethysmography sensor and the motion sensor and configured to
   filter the photoplethysmography signal, and
   use the photoplethysmography signal, the pressure signal, and the motion signal to determine a measurement of respiration, the measurement of respiration relating to central venous pressure.

14. A non-invasive system for measuring central venous pressure, the system comprising:
   a photoplethysmography sensor and a pressure sensor adapted to be placed on a patient's skin;
   wherein the photoplethysmography sensor generates a photoplethysmography signal, and the pressure sensor generates a pressure signal which comprises an element for determining central venous pressure information;
   an accelerometer which generates one or more accelerometer signals comprising indications of the position, angle and movement of the patient; and
   an acquisition signal processing quantification module in communication with the photoplethysmography sensor and the motion sensor and configured to
   filter the photoplethysmography signal, and
   use the photoplethysmography signal, the pressure signal, and the motion signal to determine a measurement of respiration, the measurement of respiration relating to central venous pressure.

* * * * *

UNITED STATES PATENT AND TRADEMARK OFFICE
CERTIFICATE OF CORRECTION

PATENT NO. : 8,721,555 B2
APPLICATION NO. : 12/708403
DATED : May 13, 2014
INVENTOR(S) : Philip R. Westbrook et al.

Page 1 of 1

It is certified that error appears in the above-identified patent and that said Letters Patent is hereby corrected as shown below:

On the Title Page

On page 2, in column 2, under "Other Publications", line 30, delete "Benum0f." and insert -- Benumof. --, therefor.

On page 2, in column 2, under "Other Publications", line 32, delete "Arnerica," and insert -- America, --, therefor.

On page 3, in column 1, under "Other Publications", line 19, delete "Bariactric" and insert -- Bariatric --, therefor.

On page 3, in column 1, under "Other Publications", line 25, delete "Apnear" and insert -- Apnea --, therefor.

In the Claims

In column 13, line 9, in claim 1, delete "information" and insert -- information; --, therefor.

In column 14, line 10, in claim 11, after "acquisition" delete "of".

In column 14, line 16, in claim 12, after "quantification" delete "signal".

In column 14, line 40-41, in claim 13, after "signal," delete "and".

In column 14, line 41, in claim 13, delete "signal" and insert -- signal, and the position signal --, therefor.

In column 14, line 57, in claim 14, delete "motion sensor" and insert -- accelerometer --, therefor.

In column 14, line 60, in claim 14, delete "motion signal" and insert -- one or more accelerometer signals --, therefor.

Signed and Sealed this
Twenty-first Day of October, 2014

Michelle K. Lee
*Deputy Director of the United States Patent and Trademark Office*